United States Patent
Cook et al.

(10) Patent No.: US 11,160,686 B2
(45) Date of Patent: Nov. 2, 2021

(54) MULTI-CORE FIBER FOR A MULTI-SPOT LASER PROBE

(71) Applicant: Alcon Inc., Fribourg (CH)

(72) Inventors: Christopher Cook, Laguna Niguel, CA (US); Chenguang Diao, Irvine, CA (US); Mark Harrison Farley, Laguna Hills, CA (US); Alireza Mirsepassi, Irvine, CA (US); Timothy C. Ryan, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 75 days.

(21) Appl. No.: 16/218,365

(22) Filed: Dec. 12, 2018

(65) Prior Publication Data
US 2019/0175406 A1    Jun. 13, 2019

Related U.S. Application Data

(60) Provisional application No. 62/630,865, filed on Feb. 15, 2018, provisional application No. 62/622,299, (Continued)

(51) Int. Cl.
*A61F 9/008*    (2006.01)
*A61B 18/22*    (2006.01)
(Continued)

(52) U.S. Cl.
CPC .......... *A61F 9/00821* (2013.01); *A61B 18/22* (2013.01); *A61B 18/24* (2013.01);
(Continued)

(58) Field of Classification Search
CPC ..... A61F 9/00821; A61B 90/30; A61B 18/22; A61B 18/24
See application file for complete search history.

(56) References Cited

U.S. PATENT DOCUMENTS

| | | |
|---|---|---|
| 5,199,431 A | 4/1993 | Kittrell |
| 5,496,305 A | 3/1996 | Kittrell |
| (Continued) | | |

FOREIGN PATENT DOCUMENTS

| | | |
|---|---|---|
| JP | A1994014936 A | 1/1994 |
| JP | 2013048864 A | 3/2013 |
| (Continued) | | |

OTHER PUBLICATIONS

Wikipedia: "Optical Fiber", version last edited Nov. 27, 2017; web address: https://en.wikipedia.org/w/index.php?title=Optical_fiber&oldid=812403927; (downloaded May 30, 2019) (19 pages).

*Primary Examiner* — Christopher A Flory

(57) ABSTRACT

The present disclosure relates to a multi-core optical fiber cable (MCF). In some embodiments, an MCF comprises a plurality of cores, a cladding surrounding the plurality of cores, wherein a refractive index of one or more of the plurality of cores is greater than a refractive index of the cladding, and a coating surrounding the cladding, a distal end free of the coating and having a reduced diameter. The MCF also comprise an annular gap formed between the distal end of the MCF and the inner surface of the cannula, wherein the concentricity of the distal end of the MCF with the inner passage of the cannula is maintained.

11 Claims, 13 Drawing Sheets

Related U.S. Application Data filed on Jan. 26, 2018, provisional application No. 62/598,653, filed on Dec. 14, 2017, provisional application No. 62/597,550, filed on Dec. 12, 2017.

(51) Int. Cl.
| | |
|---|---|
| *G02B 6/38* | (2006.01) |
| *A61B 90/30* | (2016.01) |
| *A61B 18/24* | (2006.01) |
| *G02B 6/02* | (2006.01) |
| *G02B 6/42* | (2006.01) |
| *A61B 18/00* | (2006.01) |
| *A61B 18/20* | (2006.01) |

(52) U.S. Cl.
CPC .............. *A61B 90/30* (2016.02); *A61F 9/008* (2013.01); *A61F 9/00823* (2013.01); *G02B 6/3843* (2013.01); *G02B 6/3851* (2013.01); *G02B 6/3885* (2013.01); *A61B 2018/00779* (2013.01); *A61B 2018/208* (2013.01); *A61B 2018/2025* (2013.01); *A61B 2018/2065* (2013.01); *A61B 2018/2211* (2013.01); *A61B 2018/2255* (2013.01); *A61B 2018/2266* (2013.01); *A61B 2018/2294* (2013.01); *A61B 2090/306* (2016.02); *A61F 2009/00863* (2013.01); *G02B 6/02042* (2013.01); *G02B 6/4206* (2013.01)

(56) References Cited

U.S. PATENT DOCUMENTS

| | | | |
|---|---|---|---|
| 5,625,638 A | 4/1997 | Trost | |
| 5,693,043 A | 12/1997 | Kittrell | |
| 5,921,981 A | 7/1999 | Bahmanyar et al. | |
| 6,066,128 A | 5/2000 | Bahmanyar et al. | |
| 6,096,028 A | 8/2000 | Bahmanyar et al. | |
| 6,893,432 B2 | 5/2005 | Intintoli et al. | |
| 7,189,226 B2 | 3/2007 | Auld et al. | |
| 7,302,142 B2 | 11/2007 | Conde | |
| 7,327,922 B2* | 2/2008 | Skovgaard | G02B 6/02357 |
| | | | 385/125 |
| 7,448,995 B2 | 11/2008 | Wiklof | |
| 7,450,806 B2* | 11/2008 | Bookbinder | C03B 37/01446 |
| | | | 385/125 |
| 7,526,166 B2* | 4/2009 | Bookbinder | G02B 6/02366 |
| | | | 385/123 |
| 7,539,382 B2* | 5/2009 | Skovgaard | G02B 6/02357 |
| | | | 385/125 |
| 7,566,173 B2 | 7/2009 | Auld et al. | |
| 8,398,240 B2 | 3/2013 | Smith | |
| 8,488,930 B2 | 7/2013 | Papac | |
| 8,498,506 B2 | 7/2013 | Smith | |
| 8,561,280 B2 | 10/2013 | Diao et al. | |
| 8,571,364 B2 | 10/2013 | Smith | |
| 8,764,261 B2 | 7/2014 | Smith | |
| 8,903,475 B2 | 12/2014 | Brennan et al. | |
| 8,939,964 B2 | 1/2015 | Smith | |
| 8,951,244 B2 | 2/2015 | Smith | |
| 8,968,347 B2 | 3/2015 | McCollam | |
| 9,055,885 B2 | 6/2015 | Horvath | |
| 9,107,730 B2 | 8/2015 | Huculak et al. | |
| 9,211,214 B2 | 12/2015 | Rubinchik | |
| 9,308,128 B2 | 4/2016 | Smith | |
| 9,364,982 B2 | 6/2016 | Schaller | |
| 9,387,040 B2 | 7/2016 | Smith | |
| 9,402,643 B2 | 8/2016 | Auld | |
| 9,681,793 B2 | 6/2017 | Artsyukhovich | |
| 10,012,800 B2 | 7/2018 | Diao | |
| 10,016,302 B2 | 7/2018 | Shazly | |
| 10,111,778 B2 | 10/2018 | Smith | |
| 10,245,181 B2 | 4/2019 | Diao | |
| 10,433,718 B2 | 10/2019 | Liolios | |
| 10,441,157 B2 | 10/2019 | Smith | |
| 10,838,155 B2* | 11/2020 | Kopp | G02B 6/12016 |
| 10,989,866 B2* | 4/2021 | Lyngsoe | C03B 37/0122 |
| 2001/0012429 A1* | 8/2001 | Wach | G02B 6/12007 |
| | | | 385/115 |
| 2002/0045811 A1 | 4/2002 | Kittrell | |
| 2002/0118908 A1* | 8/2002 | Conde | C03C 27/06 |
| | | | 385/14 |
| 2002/0138073 A1* | 9/2002 | Intintoli | A61B 18/22 |
| | | | 606/15 |
| 2004/0236183 A1 | 11/2004 | Durell | |
| 2005/0215987 A1* | 9/2005 | Slatkine | A61B 18/203 |
| | | | 606/9 |
| 2006/0184162 A1 | 8/2006 | Smith | |
| 2008/0051770 A1 | 2/2008 | Scheller et al. | |
| 2008/0159702 A1* | 7/2008 | Skovgaard | G02B 6/02366 |
| | | | 385/125 |
| 2008/0177257 A1 | 7/2008 | Smith et al. | |
| 2008/0181567 A1* | 7/2008 | Bookbinder | G02B 6/02366 |
| | | | 385/127 |
| 2008/0215041 A1 | 9/2008 | Zemmouri | |
| 2008/0243108 A1 | 10/2008 | Murakami | |
| 2009/0270850 A1 | 10/2009 | Zhou | |
| 2009/0287196 A1 | 11/2009 | Zelickson | |
| 2009/0287197 A1 | 11/2009 | Hanley | |
| 2010/0027943 A1 | 2/2010 | Armani | |
| 2010/0228238 A1* | 9/2010 | Brennan | A61B 5/0073 |
| | | | 606/13 |
| 2010/0261961 A1 | 10/2010 | Scott | |
| 2011/0122366 A1 | 5/2011 | Smith | |
| 2011/0144627 A1 | 6/2011 | Smith | |
| 2011/0274398 A1* | 11/2011 | Fini | G02B 6/02042 |
| | | | 385/124 |
| 2012/0099112 A1* | 4/2012 | Alphonse | G01B 9/02021 |
| | | | 356/479 |
| 2012/0147329 A1* | 6/2012 | Papac | A61B 90/30 |
| | | | 351/213 |
| 2012/0191078 A1 | 7/2012 | Yadlowsky | |
| 2012/0330101 A1* | 12/2012 | Brennan | A61B 1/00179 |
| | | | 600/177 |
| 2012/0330102 A1* | 12/2012 | Brennan | A61B 1/00179 |
| | | | 600/177 |
| 2013/0150839 A1 | 6/2013 | Smith | |
| 2014/0180133 A1* | 6/2014 | Brennan | A61B 5/0066 |
| | | | 600/478 |
| 2014/0180264 A1 | 6/2014 | Diao et al. | |
| 2014/0194862 A1 | 7/2014 | Smith et al. | |
| 2014/0200566 A1 | 7/2014 | Smith | |
| 2014/0250668 A1 | 9/2014 | Smith | |
| 2015/0025369 A1* | 1/2015 | Bhagavatula | A61B 5/6852 |
| | | | 600/425 |
| 2015/0351629 A1 | 12/2015 | Wheatley | |
| 2015/0366432 A1 | 12/2015 | Artsyukhovich | |
| 2016/0178844 A1 | 6/2016 | Griffin | |
| 2016/0252683 A1* | 9/2016 | Sasaki | G02B 6/02042 |
| | | | 385/78 |
| 2016/0374562 A1* | 12/2016 | Vertikov | A61B 1/0005 |
| | | | 600/424 |
| 2017/0363508 A1* | 12/2017 | Hayashi | G01M 11/335 |
| 2018/0055596 A1 | 3/2018 | Johnson | |
| 2018/0243136 A1 | 8/2018 | Diao | |
| 2018/0243137 A1 | 8/2018 | Diao | |
| 2018/0333304 A1 | 11/2018 | Diao | |
| 2018/0344528 A1 | 12/2018 | Farley | |
| 2019/0142544 A1 | 5/2019 | Horn | |
| 2019/0175217 A1 | 6/2019 | Cook | |
| 2019/0175273 A1 | 6/2019 | Cook | |
| 2019/0175300 A1 | 6/2019 | Horn | |
| 2019/0175404 A1 | 6/2019 | Cook | |
| 2019/0175405 A1 | 6/2019 | Diao | |
| 2019/0175407 A1 | 6/2019 | Bacher | |
| 2019/0175408 A1 | 6/2019 | Diao | |
| 2019/0207358 A1* | 7/2019 | Hasegawa | H04J 14/04 |
| 2019/0209372 A1 | 7/2019 | Farley | |
| 2019/0307527 A1 | 10/2019 | Grueebler | |

(56) References Cited

U.S. PATENT DOCUMENTS

2019/0365569 A1 12/2019 Skovgaard
2020/0107960 A1 4/2020 Bacher et al.

FOREIGN PATENT DOCUMENTS

| WO | WO9208427 A2 | 9/1992 |
| WO | WO2001037769 A1 | 5/2001 |
| WO | WO2008024848 A2 | 2/2008 |
| WO | WO2018113887 A2 | 6/2018 |

\* cited by examiner

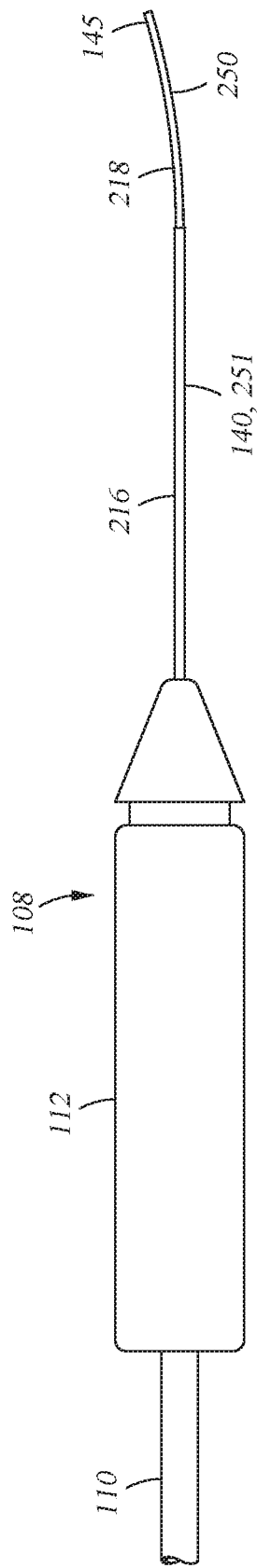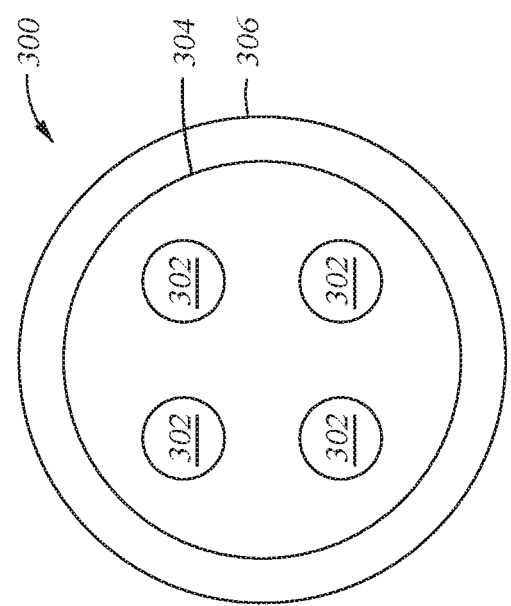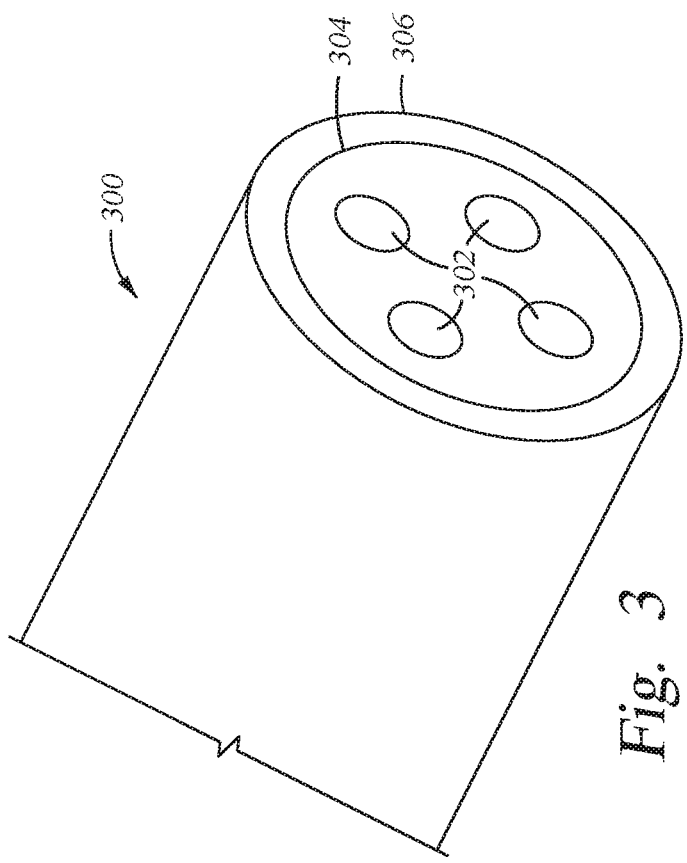
Fig. 2
Fig. 3
Fig. 4

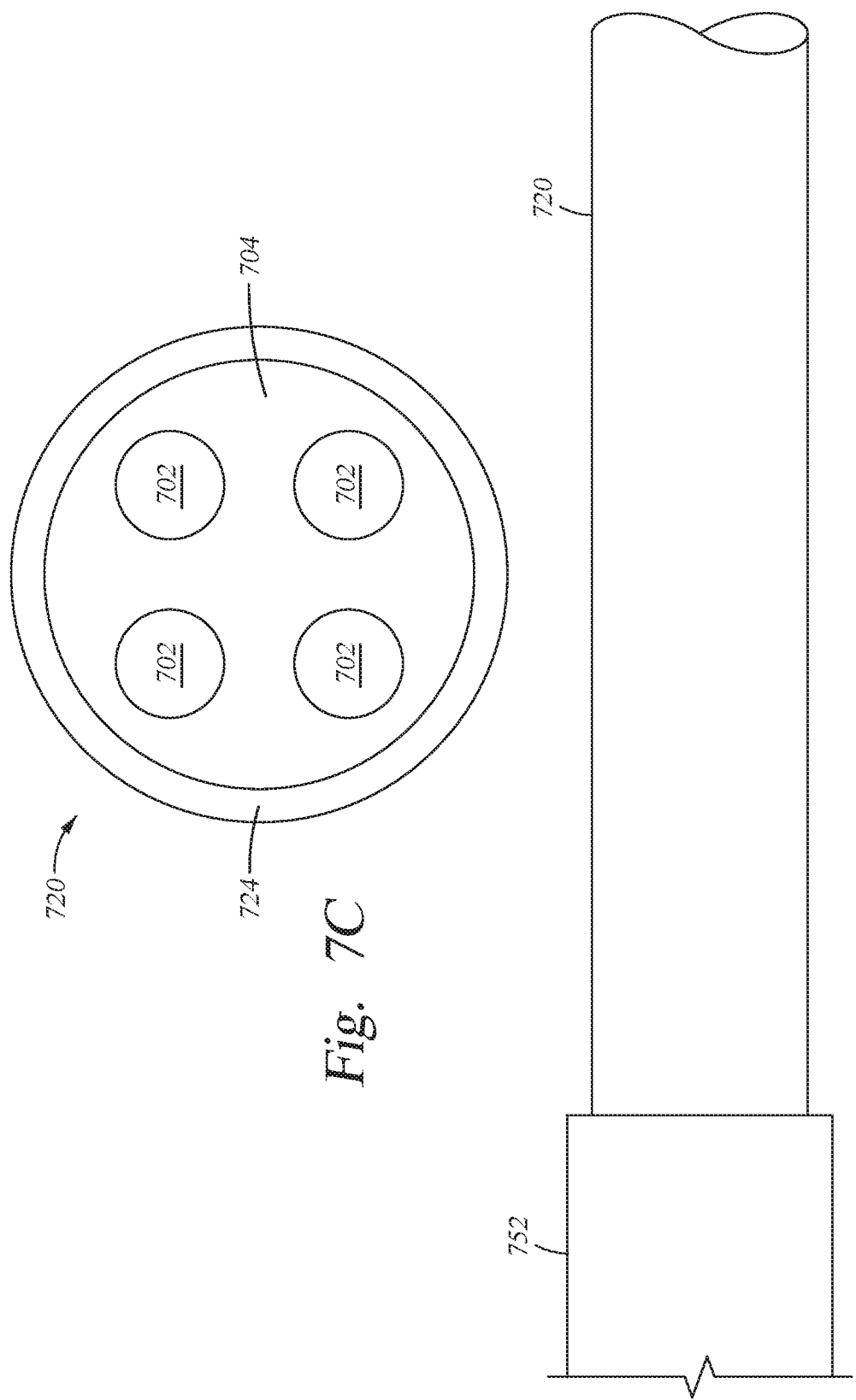

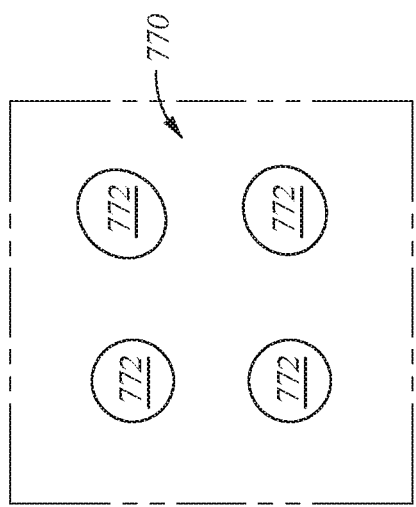
Fig. 7E2
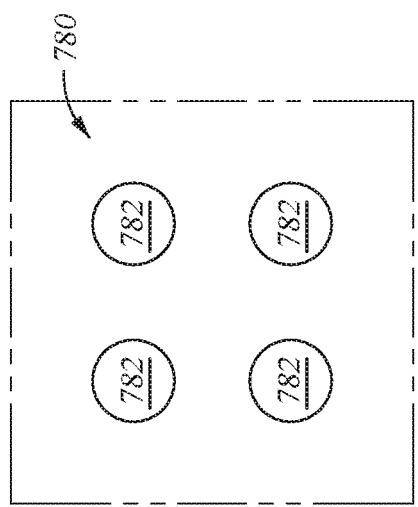
Fig. 7F2
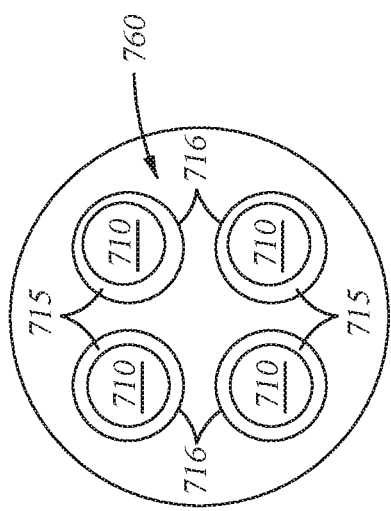
Fig. 7E1
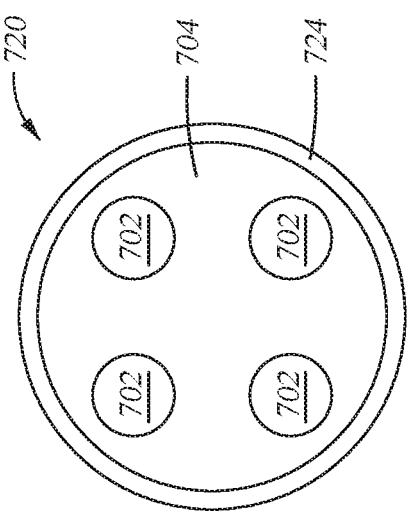
Fig. 7F1

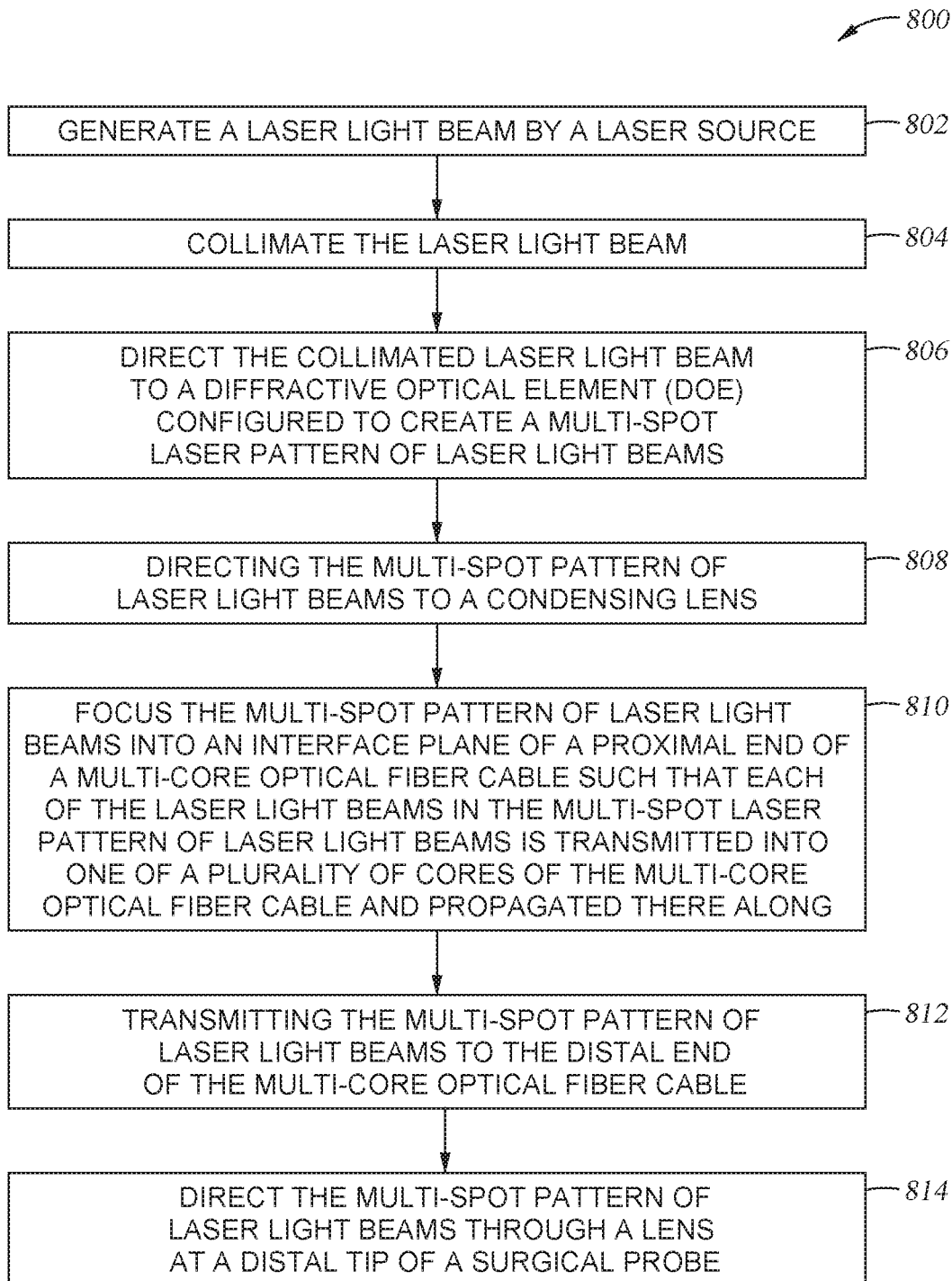

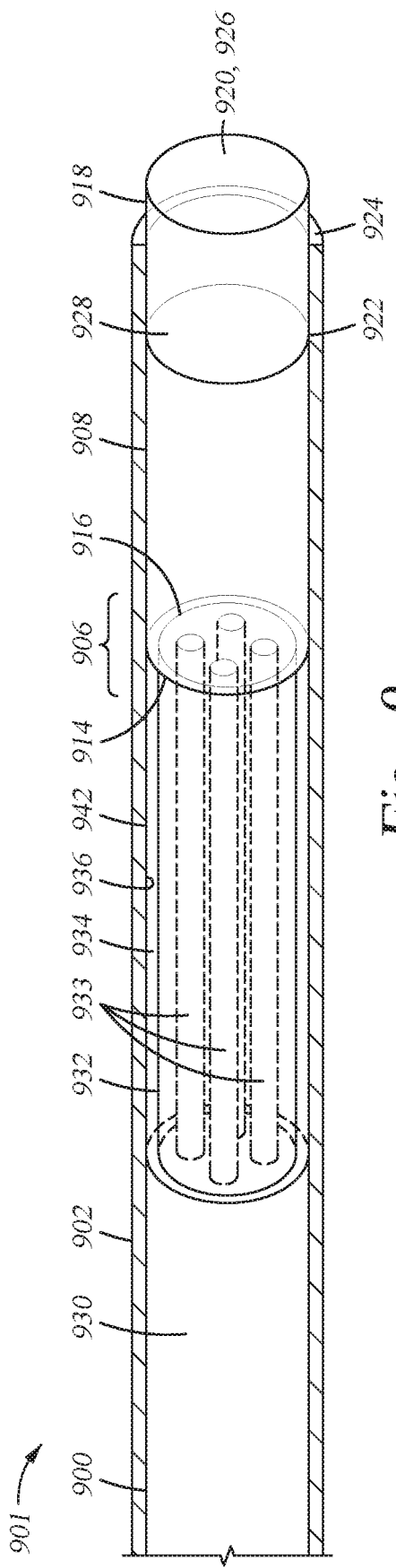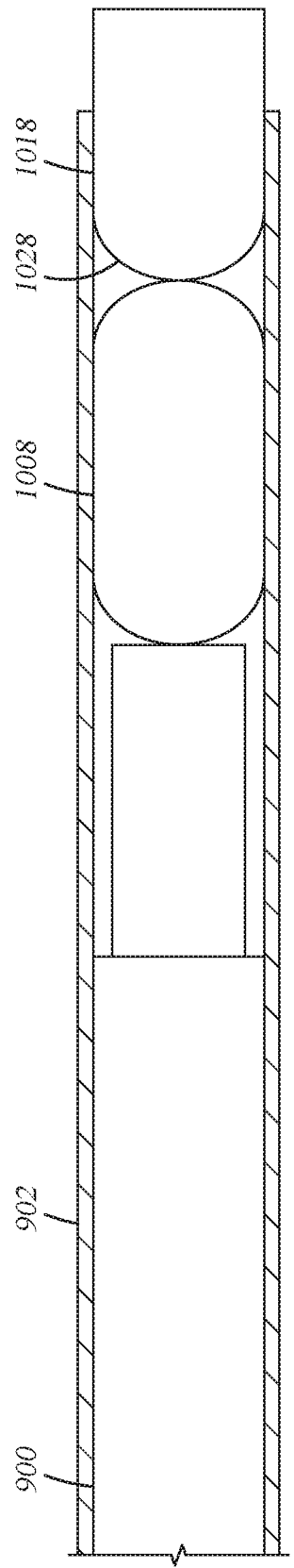
Fig. 9
Fig. 10

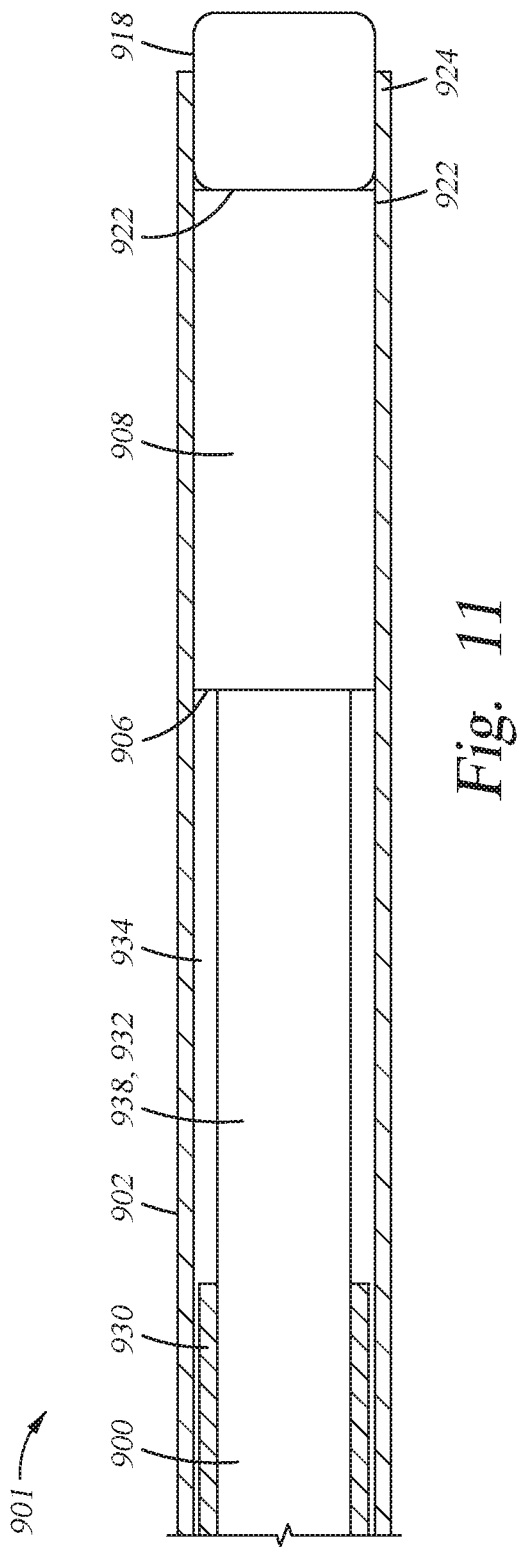
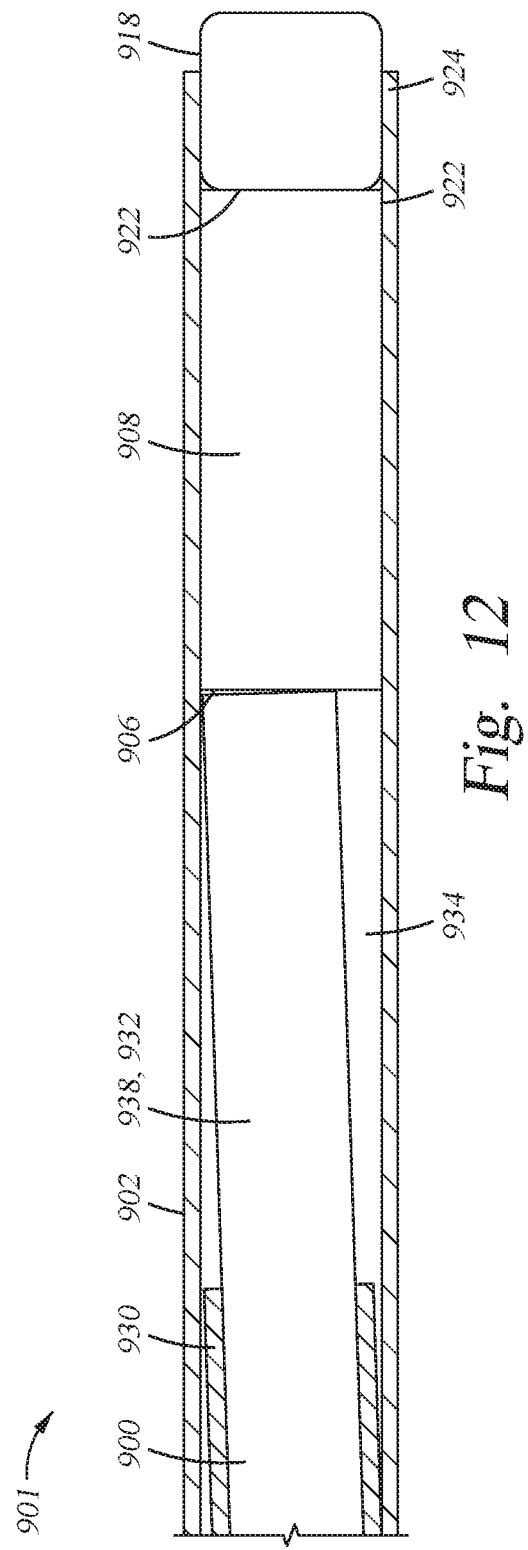

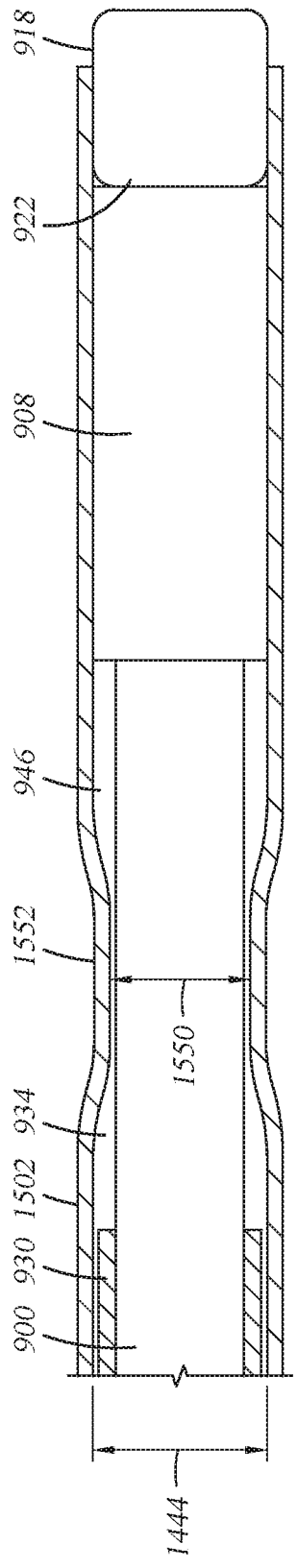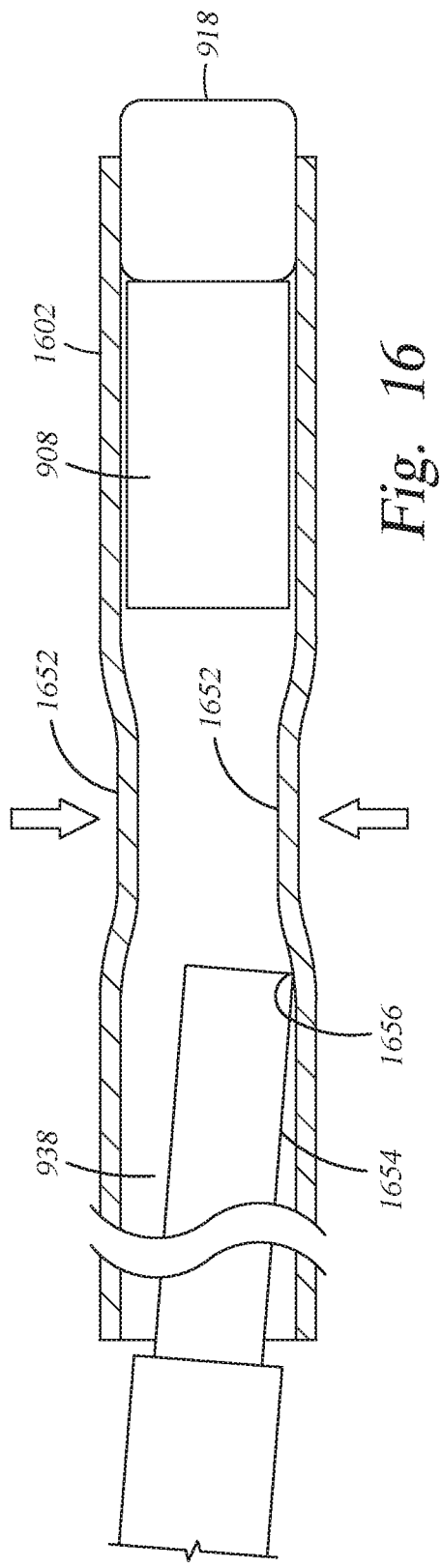

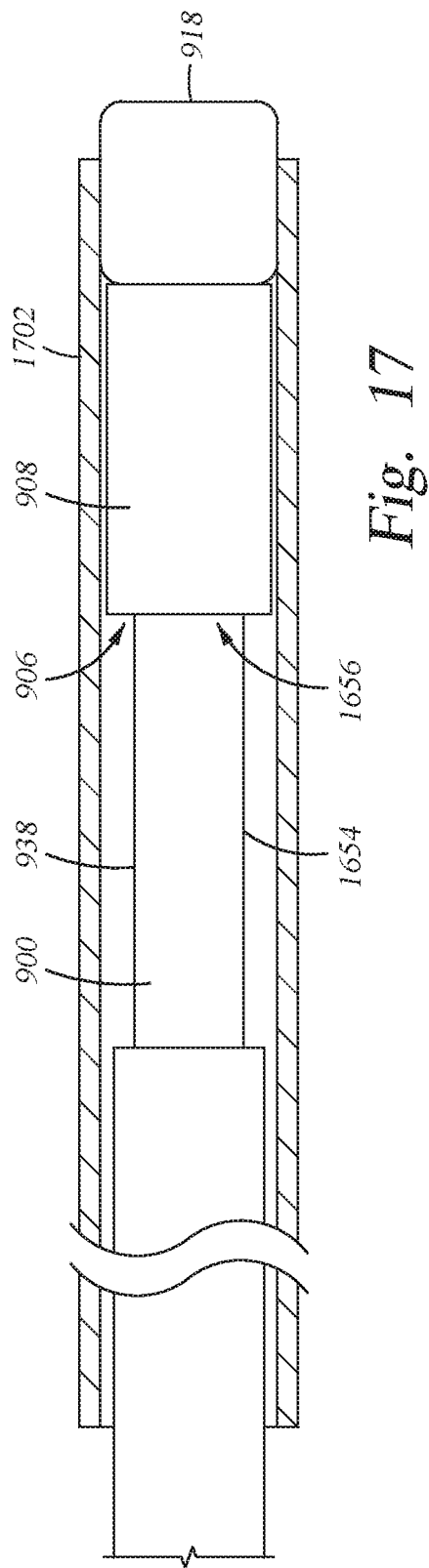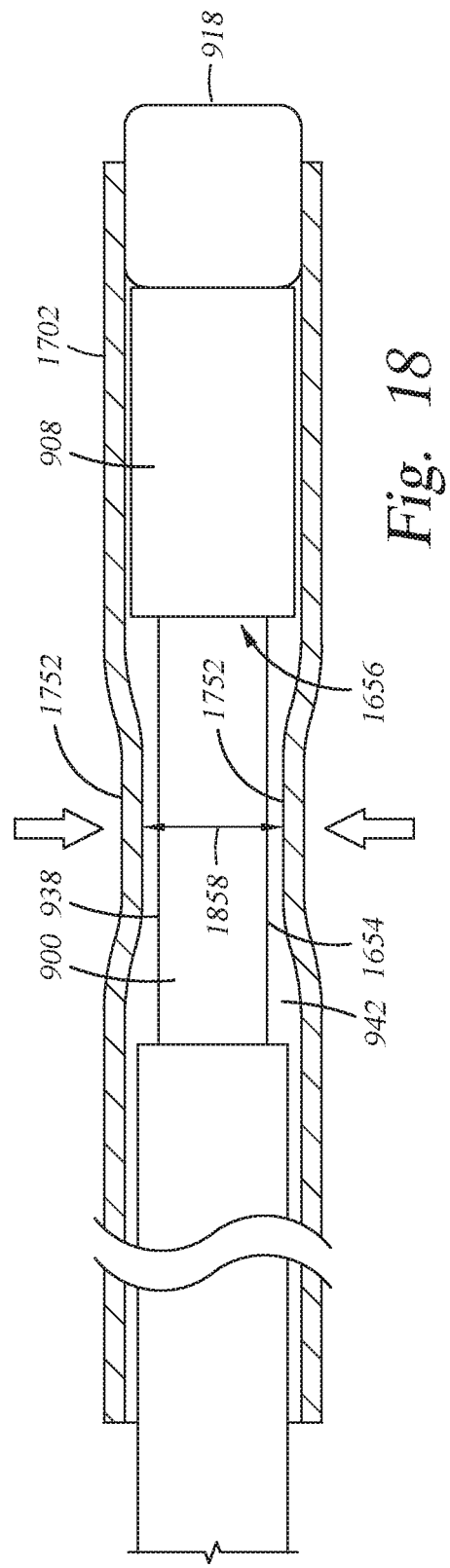

MULTI-CORE FIBER FOR A MULTI-SPOT LASER PROBE

FIELD

The present disclosure relates to a multi-spot laser probe having a multi-core optical fiber cable.

BACKGROUND

In a wide variety of medical procedures, laser light is used to assist the procedure and treat patient anatomy. For example, in laser photocoagulation, a laser probe is used to cauterize blood vessels at laser burn spots across the retina. Certain types of laser probes burn multiple spots at a time, which may result in faster and more efficient photocoagulation. Some of these multi-spot laser probes split a single laser beam into multiple laser beams that exhibit a laser spot pattern and deliver the beams to an array of optical fibers that exhibit a corresponding fiber pattern. Typically, the fibers should be tightly packed so that the fiber pattern matches the laser spot pattern. Moreover, the laser spot pattern should be accurately aligned with the fiber pattern.

In addition to cauterizing blood vessels at the laser burn spots, the laser may also damage some of the rods and cones that are present in the retina that provide vision, affecting eyesight. Since vision is most acute at the central macula of the retina, the surgeon arranges the laser probe to generate laser burn spots in the peripheral areas of the retina. In this fashion, some peripheral vision may be sacrificed to preserve central vision. During the procedure, the surgeon drives the probe with a non-burning aiming beam such that the retinal area to be photocoagulated is illuminated. Due to the availability of low-power red laser diodes, the aiming beam is generally a low-power red laser light. Once the surgeon has positioned the laser probe so as to illuminate a desired retinal spot, the surgeon activates the laser through a foot pedal or other means to then photocoagulate the illuminated area. Having burned a retinal spot, the surgeon repositions the probe to illuminate a new spot with the aiming light, activates the laser, repositions the probe, and so on until a desired number burned laser spots are distributed across the retina.

For diabetic retinopathy, a pan-retinal photocoagulation (PRP) procedure may be conducted, and the number of required laser photocoagulations for PRP is typically large. For example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, multi-spot/multi-fiber laser probes have been developed and described in U.S. Pat. Nos. 8,951,244 and 8,561,280, which are hereby incorporated by reference in their entirety.

Vitreoretinal procedures also benefit from illumination light being directed into the eye and onto retinal tissue. Vitreoretinal surgeons oftentimes use a laser probe for delivering the laser aiming beams and laser treatment beams and also use an additional instrument for directing an illumination light beam onto the retinal surface in order to view patient anatomy.

SUMMARY

According to one aspect, the present disclosure is directed to a multi-spot laser probe that includes a probe body shaped and sized for grasping by a user, a probe tip comprising a cannula configured for insertion into an eye; an annular gap formed between a distal end of the multi-core optical fiber cable (MCF) and the inner surface of the cannula, and a ring disposed within the annular gap to maintain concentricity of the distal end of the MCF with the inner passage of the cannula. The MCF may include a plurality of cores, a cladding surrounding the plurality of cores, and a coating surrounding the cladding; and the distal end. A refractive index of one or more of the plurality of cores may be greater than a refractive index of the cladding. The distal end may be free of the coating and have a reduced diameter.

Another aspect is directed to a multi-spot laser probe that includes a probe tip that includes a cannula and that is configured for insertion into an eye, a MCF and a lens. The probe cannula may include an inner passage. The passage may include a first portion defining a first inner diameter and a second portion defining a second inner diameter larger than the first diameter. The MCF may include a plurality of cores, a cladding surrounding the plurality of cores, a coating surrounding the cladding, and a distal end free of the coating and having a reduced diameter. A refractive index of one or more of the plurality of cores may be greater than a refractive index of the cladding. The distal end may extend at least partially through the first portion of the inner passage of the cannula. The lens may be disposed in the second portion of the inner passage and may be located distal of and adjacent to the distal end of the multi-core optical fiber cable.

A further aspect is directed to a method of producing a multi-spot laser probe. The method may include providing a probe tip comprising a cannula configured for insertion into an eye, inserting a lens into the cannula, inserting a MCF into the cannula proximal to the lens, and forming a necked down portion in the cannula. The MCF may include a plurality of cores, a cladding surrounding the plurality of cores, a coating surrounding the cladding, and a distal end free of the coating and having a reduced diameter. A refractive index of one or more of the plurality of cores may be greater than a refractive index of the cladding. The necked down portion may form a reduced cross-sectional size that maintains the exposed end of the MCF centered within the cannula.

The various aspects of the present disclosure may include one or more of the following features. The ring may be formed of a polyimide or a metal. An inner diameter of the ring may correspond to an outer diameter of the distal end of the multi-core optical fiber cable. An outer diameter of the ring may correspond to an inner diameter of the inner passage of the cannula. A lens may be disposed in the inner passage of the cannula distal of the multi-core optical fiber cable. The lens may be a GRIN lens. The distal end of the MCF may abut the lens with a positive pressure. The distal end of the MCF may be separated from the lens by an air gap. A window may be at least partially disposed in the inner passage of the cannula distal to and abutting the lens.

The various aspects of the present disclosure may also include one or more of the following features. A window may be at least partially disposed in the second portion of the inner passage of the cannula distal to and abutting the lens. The second portion of the inner passage may define a counter bore that extends proximally from a distal end of the cannula. The cannula may also include a crimped portion that defines the first portion of the inner passage. Forming the necked down portion may include reducing an inner diameter of the cannula such that the reduced inner diameter at the necked down portion conforms to the reduced diameter of the distal end of the multi-core optical fiber cable.

Forming the necked down portion in the cannula may include forming a crimp in the cannula. A window may be inserted into the cannula. The window may be located distal of the lens. Inserting the MCF into cannula may include abutting the distal end of the MCF and the window with positive pressure. Inserting MCF into cannula may include forming a gap between the distal end of the MCF and a proximal end of the lens.

BRIEF DESCRIPTION OF THE DRAWINGS

For a more complete understanding of the present technology, its features, and its advantages, reference is made to the following description, taken in conjunction with the accompanying drawings, in which:

FIG. 2 illustrates an example multi-spot laser probe, in accordance with a particular embodiment of the present invention.

FIGS. 3 and 4 illustrate an end of an example multi-core optical fiber cable (MCF) for use with non-illuminating multi-spot laser probes, in accordance with a particular embodiment of the present invention.

FIGS. 7A-7F2 show various aspects of multi-spot/multi-fiber laser probes in comparison with aspects of MCF laser probes to highlight various advantages and benefits of the multi-core fiber cable laser probes, in accordance with a particular embodiment of the present invention.

FIG. 8 illustrates example operations performed by a surgical laser system, in accordance with a particular embodiment of the present invention.

FIG. 9 shows a distal end portion of an example multi-spot laser probe operable to produce a multi-spot pattern of laser light beams, in accordance with a particular embodiment of the present invention.

FIG. 10 shows a distal end portion of another example multi-spot laser probe in which a lens having convex ends is disposed between a distal end of a MCF and a protective window, in accordance with a particular embodiment of the present invention.

FIG. 11 is a side view of an exposed end of an example multi-spot laser probe showing the exposed end of a MCF aligned with a lens, in accordance with a particular embodiment of the present invention.

FIG. 12 shows the exposed end of a MCF misaligned with a lens as a result of an annular gap formed between the MCF and an inner wall of a cannula.

FIG. 15 shows an example multi-spot laser probe in which alignment of an exposed end of a MCF is provided by a reduced inner diameter of a cannula, in accordance with a particular embodiment of the present invention.

FIG. 16 illustrates a potential risk of damage to a distal end of a MCF during assembly, in accordance with a particular embodiment of the present invention.

FIGS. 17 and 18 illustrate formation of a necked down portion of a cannula of an example multi-spot laser probe to maintain alignment of a distal end of a MCF and a lens, in accordance with a particular embodiment of the present invention.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described example is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 1:
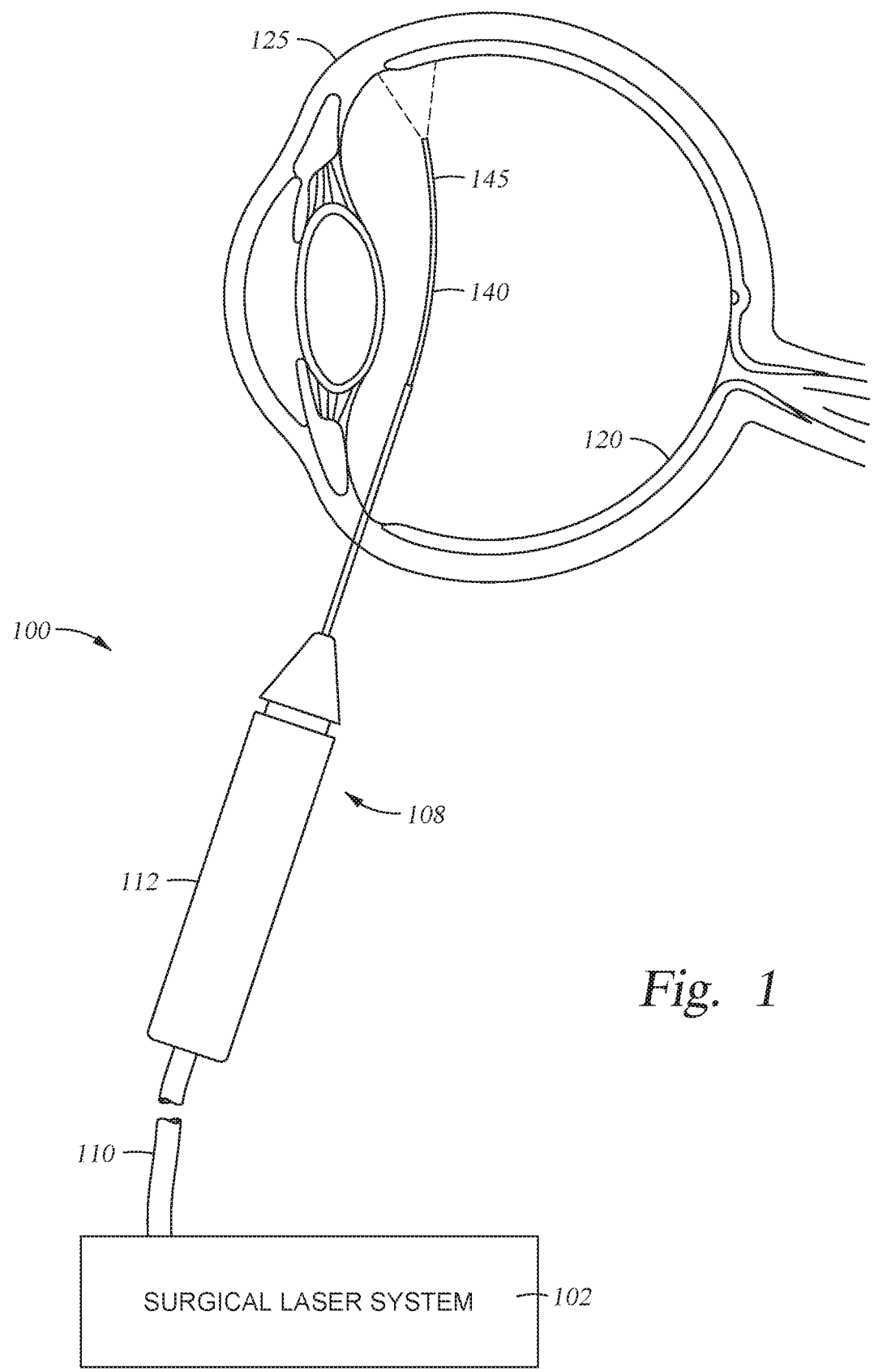
FIG. 1 illustrates an example system for generating a multi-spot pattern of laser light beams for delivery to a surgical target, in accordance with a particular embodiment of the present invention.

The present disclosure describes illuminating and non-illuminating multi-core laser probes and systems and methods associated therewith. FIG. 1 illustrates an example system 100 for creating a multi-spot pattern of laser light beams, according to certain embodiments.

System 100 includes a surgical laser system 102 that includes one or more laser sources for generating laser beams that may be used during an ophthalmic procedure. For example, the ophthalmic surgical laser system 102 can alternatively generate a surgical treatment beam with a first wavelength (e.g., ~532 nanometers (nm)) and a laser aiming beam with a second wavelength (e.g., ~635 nm). A user, such as a surgeon or surgical staff member, can control the surgical laser system 102 (e.g., via a foot switch, voice commands, etc.) to alternatively emit the laser aiming beam and fire the treatment beam to treat patient anatomy, e.g., perform photocoagulation. In some instances, the surgical laser system 102 may include a port, and the laser beams may be emitted through the port in the surgical laser system 102. The surgical laser system 102 may include a laser system port adaptor containing optical elements (not shown) for creating a multi-spot pattern of laser light beams from a laser light beam from the laser source.

System 100 can deliver the multiplexed light beam from the port to a surgical probe 108 via a multi-core optical fiber cable (MCF) 110. Probe 108 may produce a multi-spot pattern of laser light beams to be delivered to the retina 120 of a patient's eye 125. Probe 108 includes a probe body 112 and a probe tip 140 that house and protect the MCF 110. A distal end portion 145 of the probe tip 140 also contains a lens (not shown, described in greater detail below) that translates the multiplexed light beam from the distal end of the MCF 110 onto the retina 120.

Various systems and methods can be employed to create a multi-spot pattern of laser light beams and to multiplex the multi-spot pattern of laser light beams with an illumination light beam. In some cases, a port adaptor may contain optical elements operable to create a multi-spot pattern and/or multiplex light beams. In some implementations, the surgical laser system 102 may also include a female chimney port (not shown), and the port adapter may include a ferrule that functions as a male coupling for the female chimney port. The ferrule may include an opening that allows laser light from surgical laser system 102 to enter and one or more optical elements to collimate laser light received from the laser source. In some examples, the optical element in the ferrule may be a graded-index (GRIN) lens with a length and a pitch selected such that the optical element collimates laser light received at the opening of the ferrule at a selected distance adjacent to a diffractive optical element (DOE). In other examples, the optical element may be one of several other types of lenses (e.g., spherical, aspherical, biconvex glass lens etc.). The DOE may focus a multi-spot pattern of laser light beams into an interface plane of a proximal end of an MCF such that each of the laser light beams in the multi-spot laser pattern of laser light beams is propagated along an entire length of a selected core of a plurality of cores contained within the MCF, to a distal end of a surgical probe.

In operation, a laser source of surgical laser system 102 generates a laser light beam. Collimating optics in the surgical laser system 102 collimate the laser light, which is directed to a diffractive optical element configured to create a multi-spot laser pattern of laser light beams. The multi-spot laser pattern is then directed to a condensing lens and focusing optics of the surgical laser system 102 to focus the multi-spot pattern onto an interface plane of a proximal end of an MCF such that each of the laser light beams in the multi-spot laser pattern of laser light beams is propagated along an entire length of a selected core of a plurality of cores contained within the MCF 110. The multi-spot pattern of laser light beams is transmitted by MCF 110 to probe 108 disposed at a distal end of the MCF 110. The multi-spot pattern of laser light beams exits the MCF 110 and is transmitted through a lens at distal end portion 145 of the probe 108. The multi-spot pattern of laser light beams exiting the probe 108 may be projected onto the retina 120 of eye 125.

FIG. 2 illustrates embodiments of probe tip 140 of FIG. 1 in more detail. As described above, the probe 108 includes a probe body 112 shaped and sized for grasping by a user. Extending from the probe body 112 is probe tip 140, which includes a sleeve 251 and a cannula 250. As shown, cannula 250 is partially housed by and extends beyond the distal end of sleeve 251. In the illustrated example, the probe tip 140 includes a straight portion 216 (e.g., sleeve 251 and a straight part of cannula 250) and a curved portion 218 (e.g., the curved part of cannula 250). In other implementations, the probe tip 140 may have other shapes. For example, in some instances, the probe tip 140 may be entirely straight, include more than one curved portion, be entirely curved, or be shaped in any desired manner.

Probe tip 140 may be formed of one or more materials including, for example, stainless steel, titanium, Nitinol, and platinum. In some examples, a first portion of probe tip 140 (e.g., the straight portion 216) may include a first material and a second portion of probe tip 140 (e.g., curved portion 218) may include a second material. In some instances, the first material may be different from the second material. For example, in some instances, the first material may include stainless steel, e.g., tubular stainless steel, and the second material may include Nitinol, e.g., tubular Nitinol. A distal end portion 145 of the probe tip 140 may be inserted into an eye to perform a surgical procedure.

FIGS. 3 and 4 illustrate the distal end of an example MCF 300 (e.g., similar to MCF 110) from different angles. The MCF 300 includes a plurality of cores 302 disposed in a cladding 304, which may be formed from fused silica. Laser light provided by a laser light source, such as the surgical laser system 102, discussed above, may be split into a plurality of beams. Each of the beams is directed into one of the cores 302 of the MCF 300. Thus, each of the cores 302 conducts one of the light beams along the length of the MCF 300. In some implementations, the cores 302 may be constructed, e.g., from germanium-doped silica, and the cladding 304 may be constructed from fused silica, such that the laser light traveling along the cores 302 is contained within the cores 302 and prevented from escaping from the cores 302 into the cladding 304. For example, the refractive index of the one or more of the cores 302 may be greater than the refractive index of the cladding 304.

Although four cores 302 are shown in the illustrated example, the scope of the disclosure is not so limited. Rather, in other implementations, the MCF 300 may include fewer cores 302, while other implementations may include more than four cores 302. In some implementations, the MCF 300 may include two, four, or more inner cores 302, and, in some examples, the cores 302 may form a 2×2 array that matches a 2×2 multi-spot pattern generated by a diffractive optical element that may be disposed in a surgical laser system, such as surgical laser system 102. A coating 306 is formed over the cladding 304. In some instances, the coating 306 may be a polyimide coating. In other instances, the coating 306 may be formed from other materials, such as acrylate. In some implementations, an index of refraction of the coating 306 may be greater than, less than, or the same as the index of refraction of the cladding 304.

In certain embodiments, the diameter of each core 302 may be about 75+/−2 µm, the outer diameter of the cladding 304 may be about 295+/−5 microns (µm), and the outer diameter of the coating 506 may be about 325+/−5 µm. In certain embodiments, the centers of two adjacent cores 302 may be about 126+/−5 µm from each other while the distance between the centers of two cores 302 that are diagonal with respect to each other may be about 178+/−5 µm.

In the example of FIGS. 3 and 4, the MCF 300 is a non-illuminating MCF. That is, while each of the cores 302 is adapted to conduct light, e.g., laser light, the cladding 304 itself is not utilized to conduct a light used for general illumination at the treatment site.

Figure 5:
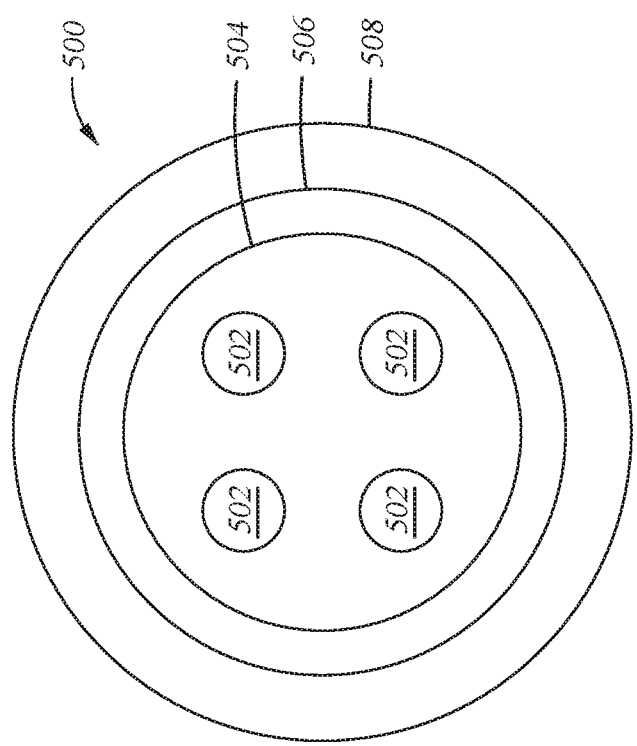
FIG. 5 shows an end of an example MCF for use with illuminating multi-spot laser probes, in accordance with a particular embodiment of the present invention.

FIG. 5 shows an example of an illuminating MCF, shown as MCF 500. The MCF 500 includes a plurality of cores 502 disposed in an inner cladding 504, which may be formed from fused silica. The cores 502 operate similarly to the cores 302 described above. Although four cores 502 are shown in the illustrated example, the scope of the disclosure is not so limited. Rather, in other implementations, the MCF 500 may include fewer cores 502, while other implementations may include more than four cores 502. In some implementations, the MCF 500 may include two, four, or more inner cores 502, and, in some examples, the cores 502 may form a 2×2 array that matches a 2×2 multi-spot pattern generated by a diffractive optical element that may be disposed in a surgical laser system, such as surgical laser system 102. An outer cladding 506 is formed over the inner cladding 504. The MCF 500 also includes a coating 508 formed over the outer cladding 506. Coating 508 may refer to a jacket. In some instances, the outer cladding 504 and the coating 508 may be formed from a polymeric material.

An illuminating MCF is one in which light for general illumination, as opposed to targeted laser light for treatment, is transmitted through the cladding of the MCF in order to provide general illumination at a treatment site. Thus, the inner cladding 504 may be utilized to transmit light therealong to provide general illumination, as opposed to laser light for treatment, at a treatment site. In an illuminating MCF 500, an index of refraction of the outer cladding 506 may be less than a refractive index of the inner cladding 504. The outer cladding 506, which may be a hard silica cladding, may be formed from a polymeric material that may not be stable at high temperatures. Therefore, a portion of the outer cladding 506 may be stripped or otherwise removed from the MCF 500 near an interface (e.g., about 0.5 to 5 mm) with a lens, as described below, in order to improve the power handling capability of a probe in which the MCF 500 is included. In certain embodiments, the coating 508 is removed for a length of about 50 millimeters (mm), measured from the distal end of MCF 500. This length may correspond to the length of the cannula (e.g., cannula 250). Coating 508 may be removed to allow MCF 500 to fit into the cannula because, with the coating 508 on, MCF 500 may have a larger outer diameter than the inner diameter of the cannula.

In certain embodiments, the diameter of each core 502 may be around 75+/−2 μm, the outer diameter of the inner cladding 504 may be 295+/−5 μm, the outer diameter of the outer cladding 506 may be 325+/−5 μm, and the outer diameter of the coating 508 may be 425+/−30 μm. In certain embodiments, the centers of two adjacent cores 502 may be around 126+/−5 μm from each other while the distance between the centers of two cores 502 that are diagonal with respect to each other may be around 178+/−5 μm.

Figure 6:
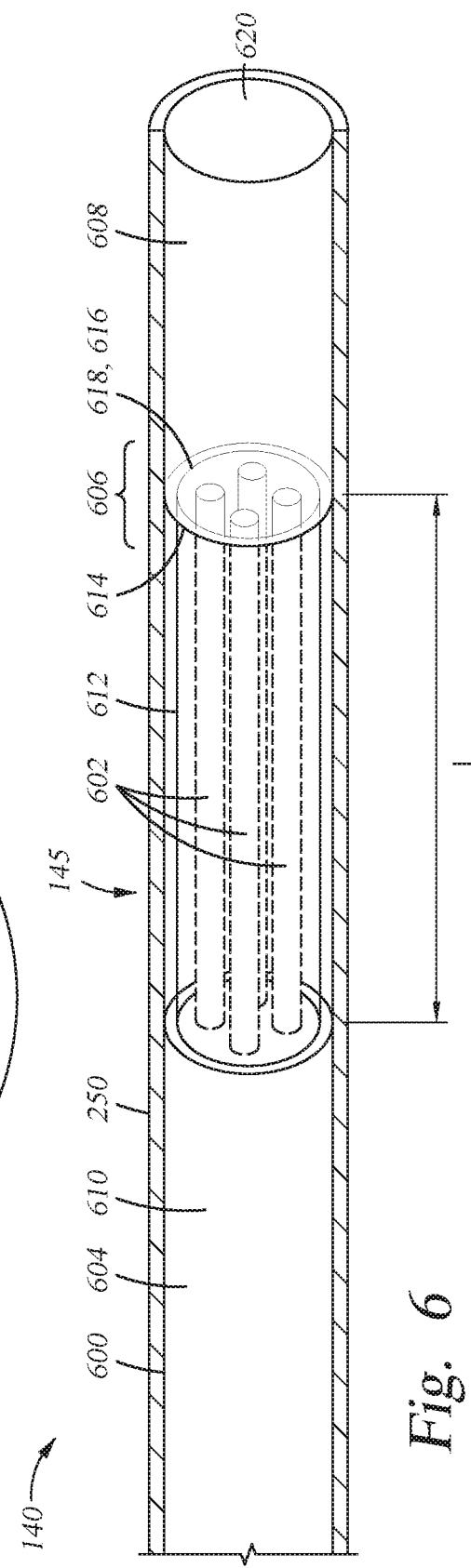
FIG. 6 is a partial cross-sectional detail view of a distal end portion of an example multi-spot laser probe tip, in accordance with a particular embodiment of the present invention.

FIG. 6 is a partial cross-sectional detailed view of the distal end portion 145 of the probe tip 140, shown in FIG. 2. Note that the distal end portion 145 of the probe tip 140 may also be the distal end portion of cannula 250. As described above, the probe tip 140, which includes cannula 250, may be formed from one or more materials, such as, for example, stainless steel, titanium, Nitinol, or platinum. An MCF 600, which may be an illuminating MCF (e.g., MCF 500, described above) or non-illuminating MCF (e.g., MCF 300, described above), extends through the cannula 250 of the probe tip 140 and includes a plurality of cores 602, which may operate similarly to cores 302 and 502 of FIGS. 3 and 5, respectively. In the illustrated example, the MCF 600 includes four cores 602, although, as explained above, the MCF 600 may include fewer or additional cores, for example, to provide a desired number of laser beams. For the purposes of illustration, the MCF 600 is described as a non-illuminating MCF. However, the scope of the disclosure also includes illuminating MCFs.

A distal end portion 604 of the MCF 600 is disposed at the distal end portion 145 of the probe tip 140 and is described in more detail, below. The distal end portion 604 terminates at an interface 606 with a lens 608. The interface 606 may be configured to translate a geometry of a multiplexed multi-spot laser pattern from the distal end of the MCF 600, through the lens 608, and onto a target surface, e.g., a tissue at a treatment site.

A portion of an outer cladding 610 of the MCF 600 is removed (e.g., by stripping), at a distal end 616 thereof, thereby exposing cladding 612. Consequently, at the interface 606, the cladding 612 of the MCF 600 is exposed. In some instances, the outer cladding 610 may be removed or omitted for a length L measured from a distal end 616 of the MCF 600 in order to mitigate or eliminate thermal problems (e.g., temperature build-up at the MCF 600 and lens 608 interface), thereby improving performance of the laser probe. For example, removal of the outer cladding 610 at the interface 606 between the MCF 600 and the lens 608 improves power handling characteristics of probe 108. That is, by removal of the outer cladding 610, the power level of the laser light passing through the probe 108 may be greater than a power level of laser light capable of being passed through the probe 108 if the outer cladding 610 were not removed from the MCF 600 at the interface 606. Consequently, with the outer cladding 610 removed as described, a higher thermal loading of the probe 108, and particularly at the interface 606, is possible In some instances, the length L may be within a range of 0.5 mm to 5.0 mm. In some instances, the length L may be within a range of 1.0 mm to 3.0 mm and any length therein. Particularly, in some instances, the length L may be 1.0 mm, 1.5 mm, 2.0 mm, 2.5 mm, or 3.0 mm. Further, the length L may be any length in between these values. At the interface 606, a distal end face 618 of the MCF 600 may abut the proximal end face 614 of the lens 608. In other instances, the distal end face 618 of the MCF 600 may be offset from the proximal face 614 of the lens 608.

In certain implementations, the distal end face 618 formed at the distal end 616 of MCF 600 may abut the proximal end face 614 of the lens 608 with positive pressure. In other implementations, the distal end face 618 of the MCF 600 may be separated from the proximal end face 614 of the lens 608 by an air gap. In still other implementations, one or more optically transmissive elements or materials may be situated at the interface 606 between the MCF 600 and the lens 608. In some implementations, the lens 608 may be a GRIN lens, a spherical lens, or an aspherical lens. In still other implementations, the lens 608 may be a group of lenses formed of optically clear material.

The lens 608 may include one or more lenses formed from a visibly transparent glass or ceramic. For example, the material used to form the one or more lenses of the lens 608 may include fused silica, borosilicate, or sapphire. In some implementations, the lens 608 may include a single-element cylindrical GRIN rod lens that is operable to receive one or more laser beams from distal end 616 of MCF 600 and relay the received laser beams toward a distal tip 620 of the probe tip 140. In some instances, the distal tip 620 of the probe tip 140 may also correspond to the distal end of the lens 608. In other instances, a protective window may be disposed between the distal end of the lens 608 and a distal tip 620 of the probe tip 140. In still other implementations, the window may extend from a distal tip 620 of the probe tip 140.

While the MCF 600 is described in the context of being a non-illuminating type, the scope of the disclosure is not so limited. Rather, the concepts described herein are equally applicable to illuminating MCFs. Thus, the MCF 600 may be an illuminating MCF similar to the MCF 500 of FIG. 5.

Figure 7A:
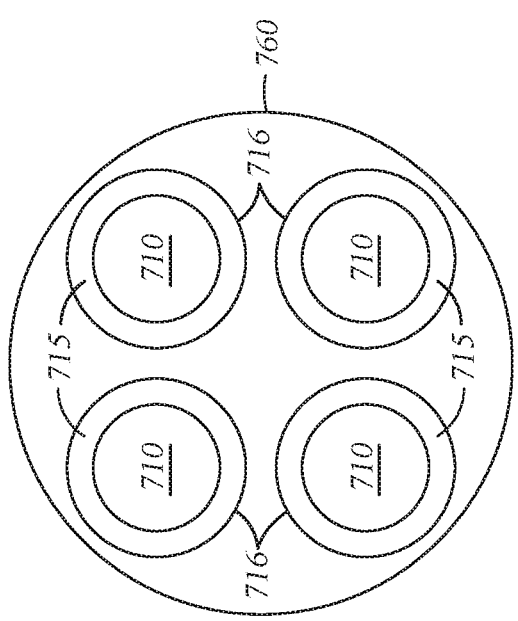
Figure 7B:
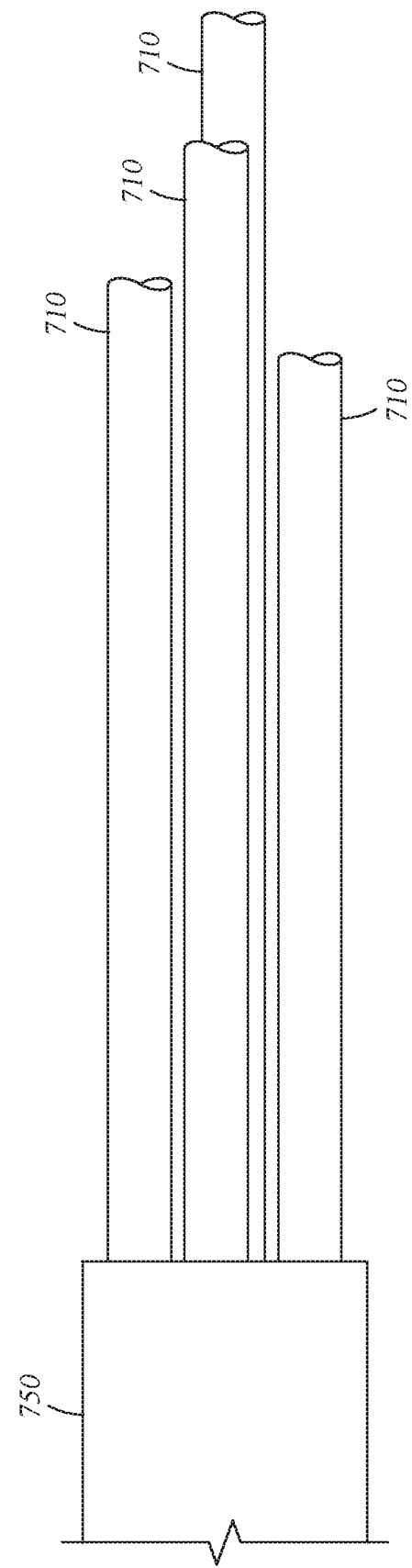

FIGS. 7A-D, E1-E2, and F1-F2 compare embodiments of a multi-spot/multi-fiber laser probe with an MCF laser probe, as disclosed herein, to highlight various advantages and benefits of the MCF laser probe. FIGS. 7A-7B illustrate multiple fibers 710 that may be used in a multi-spot/multi-fiber laser probe (not shown), where each of the fibers 710 is used to conduct a single laser beam. More particularly, FIG. 7A illustrates a front view of fibers 710 housed within a multi-lumen tube 760 (e.g., a micro spacer). As shown, multi-lumen tube 760 comprises four tunnel-shaped passages or holes 716, each of which houses a fiber 710. Adhesive 715 is used to bond each fiber 710 to its corresponding hole 716. FIG. 7B illustrates a side view of fibers 710 extending from a cannula 750. Note that the multi-lumen tube of FIG. 7A is not shown in FIG. 7B.

As a general matter, it is difficult to control multiple individual fibers 710 with precision during manufacturing of a multi-spot/multi-fiber laser probe. Multi-spot/multi-fiber laser probe designs can require precise alignment of multiple individual fibers 710 in the internal diameter (ID) of a ferrule to receive the multiple laser beams with the required high coupling efficiency. For example, a polyimide tube is used to manage multiple individual fibers 710, and each fiber 710 is stripped individually, which can be time-consuming. After stripping, the multiple fibers 710 are inserted into corresponding holes in the multi-lumen tube 760, which can be difficult and slow. Further, the fibers 710 are cleaved individually, retracted back to the polyimide tube and the multi-lumen tube 760, made flush by a stopper, and bonded together by UV during adhesive. The assembly then undergoes secondary heat curing to improve bonding stability at high temperature. This manufacturing process associated with the multi-spot/multi-fiber design is complicated and slow. Also the adhesive 715 used between individual fibers and their corresponding holes or housings 716 in the multi-lumen tube 760 may be prone to thermal damage and can induce probe failure.

In contrast to FIGS. 7A and 7B, FIGS. 7C and 7D illustrate an MCF 720, similar to the MCFs 300, 500, and 600 shown in FIGS. 4-6. More particularly, FIG. 7C illustrates a front view of MCF 720, which comprises a plurality of cores 702 embedded in a cladding 704, which is coated by coating 724. FIG. 7D illustrates a side view of MCF 720 extending from cannula 752. As shown, in contrast to the multiple fibers 710 of a multi-spot/multi-fiber laser probe, MCF 720 is a single fiber having a plurality of cores 702, each transmitting a laser beam.

Laser probes incorporating an MCF, such as MCF 720, do not require the use of adhesives between the cores 702, as the cores 702 are embedded in a cladding 704 and contained within a single optical fiber. As a result, laser probes comprising an MCF may have significantly improved power handling capabilities. Moreover, assembly of an MCF laser probe is comparatively simple, as only a single fiber needs to be aligned and handled during manufacturing. Accordingly, there is no need to use a polyimide tube and a multi-lumen tube to manage multiple individual fibers during assembly, and stripping a single MCF 720 takes considerably less time than stripping multiple individual fibers 710 of a multi-spot/multi-fiber probe.

Further, utilizing an MCF in a laser probe may allow for tightly controlling the direction of the propagated beams. More specifically, using an MCF may ensure that the beams propagated by the laser probe are tightly controlled and not pointing towards the inner surface of the cannula. A comparison between a laser beam pattern associated with multiple fibers of a multi-spot/multi-fiber laser probe and a laser beam patter associated with the cores of an MCF is illustrated in FIGS. 7E1-E2 and 7F1-F2.

FIG. 7E1 depicts a fiber pattern at the distal end of a fiber assembly, including multiple fibers 710, within a multi-lumen tube 760. FIG. 7E2 illustrates a laser beam pattern 770 including laser beam spots 772 corresponding to the fiber pattern of FIG. 7E1. As shown, some of fibers 710 (e.g., top and bottom right cores) are not centered within passages 716 of the multi-lumen tube 760, which result in those fibers 710 propagating beams that may be skewed outwardly, as shown in FIG. 7E2. In some cases, some of fibers 710 may not be centered within their corresponding passages 716 due to loose tolerance between the outer diameter of the fibers 710 and the inner diameter of passage 716 of the multi-lumen tube 760, causing fibers 710 to point towards the inner surface of the cannula (not shown) instead. As a result, beams propagated by fibers 710 also point towards the inner surface of the cannula, instead of being pointed in a straight direction and towards a patient's eye. This causes the beams to escape a lens, e.g., lens 608, of the laser probe and be absorbed by the inner surface of the cannula, which may cause the cannula to overheat. In addition, fibers 710 not being centered within their corresponding passages 716, result in an undesirable uniformity among the corresponding four beam spots.

In contrast to FIGS. 7E1-E2, FIGS. 7F1-F2 illustrate a fiber pattern and a beam pattern, respectively, associated with an MCF. FIG. 7F1 illustrates cores 702 of an MCF that are pointing in a straight direction and not skewed outwardly. This is because the cores 702 are embedded in the cladding tightly together. As a result, cores 702 are able to propagate beams spots 782, shown in beam pattern 782 of FIG. 7F2, which are also pointed in a straight direction and not towards the inner surface of the cannula (not shown) within which the MCF is housed. As such, using an MCF improves control of the laser beam pattern (e.g., a desirable uniformity among the four beam spots) of a laser probe and increases the power handling by preventing the cannula from overheating as a result of the beams pointing towards the inner surface of the cannula.

Thus, the disclosed MCF laser probe design may simplify manufacturing by eliminating complex and costly manufacturing requirements, improve power handling by eliminating adhesive failure or the introduction of contamination into the distal fiber assembly of a multi-fiber probe during bonding of distal ends of multiple fibers, increase coupling efficiency by employing a precisely-aligned MCF and avoiding difficulties associated with aligning individual fibers with multiple input laser beams in a multiple-fiber assembly, and improve control of the laser beam pattern (which also further improves power handling). These and other advantages will be apparent to one skilled in the art in view of the present disclosure.

FIG. 8 illustrates example flow chart 800, which illustrates steps in a method for applying a multi-spot laser beam pattern, in accordance with a particular embodiment of the present invention. In certain embodiments, operations 800 are performed by a system, such as surgical laser system 102 of FIG. 1, which is coupled to an MCF laser probe, such as MCF laser probe 108 of FIG. 1.

At block 802, the system generates a laser light beam by a laser source. As described above, the laser source may be a part of or be coupled to surgical laser system 102.

At block 804, the system collimates the laser light beam. A collimated laser light beam refers to a laser light beam having parallel rays.

At block 806, the system directs the collimated laser light beam to a diffractive optical element (DOE) configured to create a multi-spot laser pattern of laser light beams. DOEs, as one of ordinary skill in the art recognizes, are used for shaping and splitting laser light beams.

At block 808, the system directs the multi-spot pattern of laser light beams to a condensing lens.

At block 810, the system focuses the multi-spot pattern of laser light beams into an interface plane of a proximal end of an MCF such that each of the laser light beams in the multi-spot laser pattern of laser light beams is transmitted into one of a plurality of cores of the MCF and propagated there along, the plurality of cores being surrounded by a cladding and the cladding being surrounded by a coating, a refractive index of each of the plurality of cores being greater than a refractive index of the cladding, and a portion of the coating being omitted from a length of a distal end of the MCF.

For example, surgical laser system 102 focuses the multi-spot pattern of laser light beams into an interface plane of a proximal end of an MCF (e.g., MCF 110, MCF 300, MCF 500, MCF 600, etc.) such that each of the laser light beams in the multi-spot laser pattern of laser light beams is transmitted into one of a plurality of cores (e.g., cores 302, 502, 602, etc.) of the MCF and propagated there along, the plurality of cores being surrounded by a cladding (e.g., cladding 304, 504, 506, 612, etc.) and the cladding being surrounded by a coating (e.g., 306, 508, etc.), a refractive index of each of the plurality of cores being greater than a refractive index of the cladding, and a portion of the coating being omitted from a length (e.g., shown as length L in FIG. 6) of a distal end of the MCF.

At block 812, the system transmits the multi-spot pattern of laser light beams to the distal end of the MCF. For example, the system transmits the multi-spot pattern of laser light beams to the distal end (e.g., distal end 616) of the MCF.

At block 814, the system directs the multi-spot pattern of laser light beams through a lens (e.g., lens 608) at a distal tip (e.g., distal tip 620) of a surgical probe (e.g., probe 108).

FIG. 9 shows a distal end portion of another example probe 901 operable to produce a multi-spot pattern of laser light beams. The illustrated example probe 901 includes an illuminating MCF 900, which may be similar to the MCF 500 described above. Consequently, the probe 901 is operable to emit both general illumination for illuminating a surgical field as well as a plurality of laser beams for treating a treatment site, e.g., a retina. The probe 901 may be similar in many respects to the probe 108. As shown, the probe 901 includes a cannula 902. The cannula 902 includes an inner surface 936 that defines an inner passage 942. The MCF 900 extends through at least a portion of the cannula 902 up to a first interface 906 with a lens 908. The MCF 900 may abut the lens 908 or a gap, e.g., an air-filled gap, may be disposed between a distal end 916 of the MCF 900 and a proximal end 914 of the lens 908. In some instances, the distal end 916 of MCF 900 may abut the proximal end 914 of the lens 908 with positive pressure. In some instances, the lens 908 may be formed from fused silica, borosilicate, or sapphire. In some instances, the lens 908 may be a spherical lens. The lens 908 may be a GRIN lens, such as a single-element cylindrical GRIN rod lens that is operable to receive one or more laser beams from distal end of MCF 900 and relay the received laser beams toward a distal tip 920 of the probe 901.

The probe 901 also includes a protective window 918 extending from a second interface 922 with the lens 908. As shown in FIG. 9, the protective window 918 abuts the lens 908. In other implementations, a gap, e.g., an air-filled gap, may exist between the protective window 918 and the lens 908. In the illustrated example, the protective window 918 extends distally beyond a distal end 924 of the cannula 902, and a distal end 926 of the protective window 918 defines the distal tip 920 of the probe 901. In other implementations, the distal end 926 of the protective window 918 may be aligned with the distal end of the distal end 924 of the cannula 902 such that the distal end 924 of the cannula 902 and the distal end 926 of the protective window 918 are substantially flush. One of ordinary skill in the art recognizes that the relative positions of the end surface of the distal end 924 of the cannula 902 and the end surface of the distal end 926 of the protective window 918 may vary slightly due to manufacturing tolerances.

The protective window 918 may be formed from an optically stable and high temperature resistant material. In some instances, the protective window 918 may be formed from sapphire or quartz. In some instances, the protective window 918 may have a flat proximal end surface, as shown in FIG. 9. In other instances, the protective window 918 may have a convex proximal end surface 928. An example of such a lens is shown in FIG. 10.

In FIG. 10 lens 1008 has convex proximal and distal ends. Although the lens 1008 is elongated in the longitudinal direction, in other examples, it may instead be a spherical or ball lens. In some implementations, a lens having a flat proximal end and/or a flat distal end, such as the lens 908 shown in FIG. 9, may be used in combination with a protective window 1018 that has a convex proximal end, similar to that shown in FIG. 10. In still other implementations, a probe may include a lens that includes a convex proximal end and/or a convex distal end, e.g., a spherical lens or a lens such as that shown in FIG. 9, in combination with a protective window having a flat proximal end, such as the protective window 918 shown in FIG. 9.

Referring back to FIG. 9, the MCF 900 includes an outer cladding 930, which may be similar to the outer cladding 506 shown in FIG. 5. The outer cladding 930 is removed, e.g., stripped, from the inner cladding 932 for a length L measured and extending proximally from the distal end 916 of the MCF 900, thereby exposing the underlying inner cladding 932.

In some instances, the length L may be within a range of 0.5 mm to 5.0 mm. In some instances, the length L may be within a range of 1.0 mm to 3.0 mm and any length therein. Particularly, in some instances, the length L may b 1.0 mm, 1.5 mm, 2.0 mm, 2.5 mm, or 3.0 mm. Further, the length L may be any length in between these values. As explained above, removal of a portion of the outer cladding may improve the thermal handling properties of the probe, such that a power level of the laser energy transmitted through the probe may be increased. A portion of cores 933 extending through the inner cladding 932 is shown.

However, with a portion of the outer cladding 930 removed, an annular gap 934 exists between the inner cladding 932 and the inner surface 936 of the cannula 902. The annular gap 934 introduces a risk of misalignment between the MCF 900 and the lens 908 (i.e., the MCF 900 may become decentered from the lens 908). FIG. 11 is a side view of an exposed end 938 of the probe 901, wherein the exposed end 938 of the MCF 900 is aligned with the lens 908. The exposed end 938 of the MCF 900 is the portion of the MCF 900 from which the outer cladding 930 is removed.

FIG. 12, however, shows the exposed end 938 of the MCF 900 misaligned with the lens 908 as a result of the annular gap 934. As shown in FIG. 12, the exposed end 938 of the MCF 900 is not concentric with the lens 908. With the exposed end 938 of the MCF 900 misaligned with the lens 908, the resulting laser spot and illumination beam pattern are no longer concentric with the cannula 902. This misalignment between the MCF 900 and the lens 908 may also result in a portion of the light that is propagated for general illumination purposes and passes through the inner cladding 932 to strike the inner wall 936 of the cannula 902. This decreases the illumination efficiency of the probe 901 and results in an undesirable illumination pattern.

In certain embodiments, in order to maintain alignment between the MCF 900 and the lens 908, a ring formed from thermally-stable material may be disposed in the annular gap 934 to maintain concentricity of the MCF 900 with the inner passage of the cannula and the lens. In certain embodiments, the material may include e.g., polyimide, metal, stainless steel, nickel, silver, copper, brass, etc. Although polyimides and metals are possible materials from which the ring may be made, other materials may also be used. An example of a ring used for maintaining alignment between the MCF 900 and the lens 908 is illustrated in FIG. 13.

Figure 13:
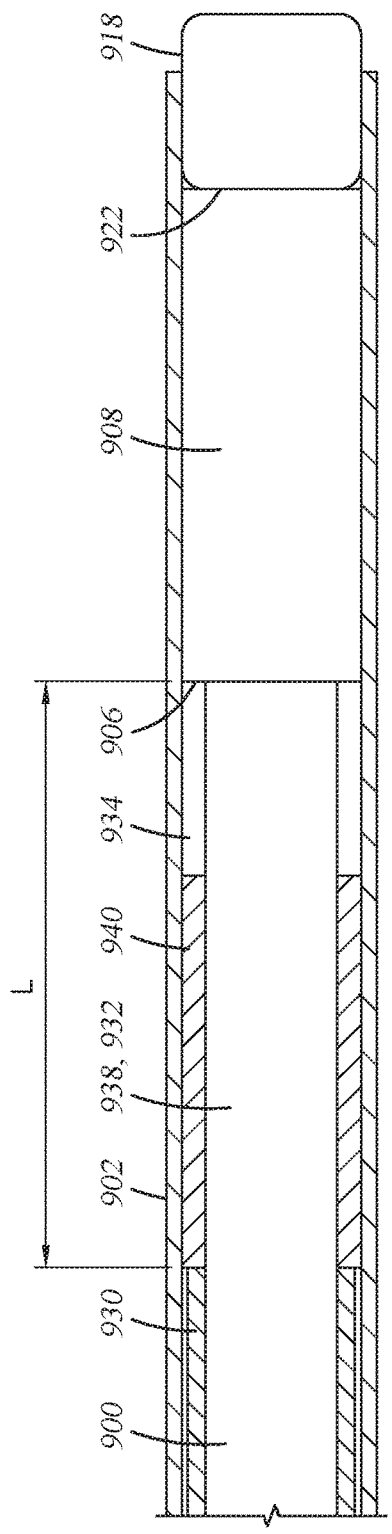
FIG. 13 shows a ring that is disposed within an annular gap formed around an inner cladding of a MCF at an exposed end thereof, in accordance with a particular embodiment of the present invention.

FIG. 13 illustrates a ring 940 disposed within the annular gap 934 formed around the inner cladding 932 at the exposed end 938 of the MCF 900. The ring 940 maintains concentricity of the MCF 900 and the lens 908, e.g., by restricting lateral movement of the exposed end 938 of the MCF 900. In some instances, the inner diameter of the ring 940 corresponds to the outer diameter of the exposed end 938 of the MCF 900. In some instances, an outer diameter of the ring 940 corresponds to an inner diameter of the inner passage 942. The ring 940 may span the entire length L of the exposed end 938 or less than the entire length L.

Figure 14:
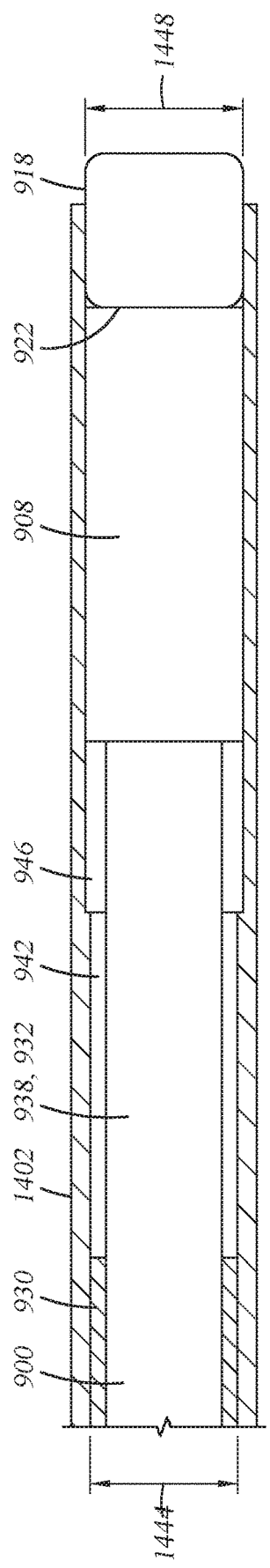
FIG. 14 shows a cannula of another example multi-spot laser probe that includes a counterbore, in accordance with a particular embodiment of the present invention.

FIG. 14 shows another example implementation for maintaining alignment of the MCF 900 and the lens 900. In the example shown in FIG. 14, the cannula 1402 includes an inner passage 942 having a first inner diameter 1444 that conforms more closely to the outer diameter of the MCF 900. The cannula 1402 also includes a counter-bore 946 having a second inner diameter 1448 larger than the first inner diameter 1444. The counter-bore 946 is provided in order to accommodate the lens 908 and the protective window 918, if included, within the cannula 1402 due to the larger transverse cross-sectional sizes of these components as compared to the transverse cross-sectional size of the MCF 900. Therefore, along the exposed end 938, the passage 942 having a reduced cross-sectional size compared to the counterbore 946 is capable of maintaining alignment of the exposed end 938 of the MCF 900 with the lens 908 to a better degree than if the inner diameter 1444 of passage 942 were the size of the inner diameter 1448 of the counter-bore 946. As a result, alignment between the MCF 900 and lens 908 is improved. In some instances, the counter-bore 946 extends proximally from the distal end of the cannula 1402.

FIG. 15 shows an example in which alignment of the exposed end 938 of the MCF 900 is provided by a reduced inner diameter 1550 of the cannula 1502. The reduced diameter 1550 is provided by a necked down portion 1552 of the cannula 1502, which may be the result of a crimp. The reduced inner diameter 1550 may be made to correspond to the outer diameter of the exposed end 938 of the MCF 900. The reduced inner diameter 1550 maintains alignment of the exposed end 938 with the lens 908, thereby achieving improved general illumination performance and alignment of the laser spot pattern with the longitudinal axis of the cannula 1502.

FIG. 16 illustrates a potential risk for introduction of damage to the MCF 900 during assembly of a multi-spot laser probe in the context of the design shown in FIG. 15. If the necked down portion 1652 of the cannula 1602, such as generated by a crimp applied to the cannula 1602, is formed prior to the introduction of the MCF 900 into necked down portion 1652, there is a risk of damage to the distal end 1654 (and particularly to the edge 1656 of the distal end 1654) of the MCF 900, when insertion of the distal end 1654 through the necked down portion 1652 is attempted. Misalignment of the distal end 1654 with the necked down portion 1652 during assembly may produce forces that can chip and damage the distal end 1654 of the MCF 900. Even small loads applied to the distal end 1654, and particularly to the edge 1656 thereof, can produce damage, such as chipping of the distal end 1654 and edge 1656, that results in an impaired performance whether in poor general illumination or an imprecise or distorted laser spot pattern or both. Such damage may render the resulting laser probe unusable. As a result, a necked down portion may be formed in a cannula after introduction of an MCF into the cannula, as shown in FIGS. 17 and 18.

FIGS. 17 and 18 show the distal end 1654 of the MCF 800 abutting the lens 908 at the first interface 906. However, as explained above, a gap may be disposed between the distal end 1654 of MCF 800 and the lens 908. In some implementations, one or both of the lens 908 and window 918 may be installed in the cannula 1702 prior to the assembly of the MCF 900. In some implementations, the MCF 900 may be installed prior to one or both of the lens 908 and window 918.

With the MCF 900 positioned within the cannula 1702 at a desired position, the necked down portion 1752 may be formed in the cannula 1702, such as by crimping. The necked down portion 1752 maintains the exposed end 938 of the MCF 900 concentric with the lens 908. As a result, the risk of the distal end 1654 of the MCF 900 being damaged by the necked down portion 1752 is eliminated.

In some instances, the necked down portion 1752 is a reduced annulus entirely encircling the exposed end 938 of the MCF 900. As a result, the necked down portion 1752 defines a reduced diameter 1858 of the inner passage 942 that conforms to the outer diameter of the exposed end 938. In some instances, the reduced diameter 1858 of the necked down portion 1752 is the same as or slightly larger than the outer diameter of the exposed end 938. As an example, a 5 µm annular gap may be formed between the inner surface of the cannula 1702 at the necked down portion 1752 and the outer surface of the exposed end 938. In some embodiments, the exposed end 938 may contact the inner surface of the necked down portion 1752 at one or more locations.

In certain embodiments, the necked down portion 1752 may form diametrically opposed protrusions at one or more locations around the circumference of the cannula 1702, thereby centering the exposed end 938 of the MCF 900 with the lens 908. For example, in some instances, the necked down portion 1752 may include two sets of diametrically opposed protrusions offset 90° from each other. In certain other implementations, three or more non-diametrically opposed protrusions may be formed in the cannula to center the exposed end 938 of the MCF 900. In some instances, the protrusions may be formed along a common circumference of the cannula 1702. In other implementations, one or more of the protrusions may be longitudinally offset from one or more of the other protrusions.

Further, although the MCF 900 is described as an illuminating MCF, in some implementations, the MCF 900 may be non-illuminating MCF and remain within the scope of the disclosure.

Figure 19:
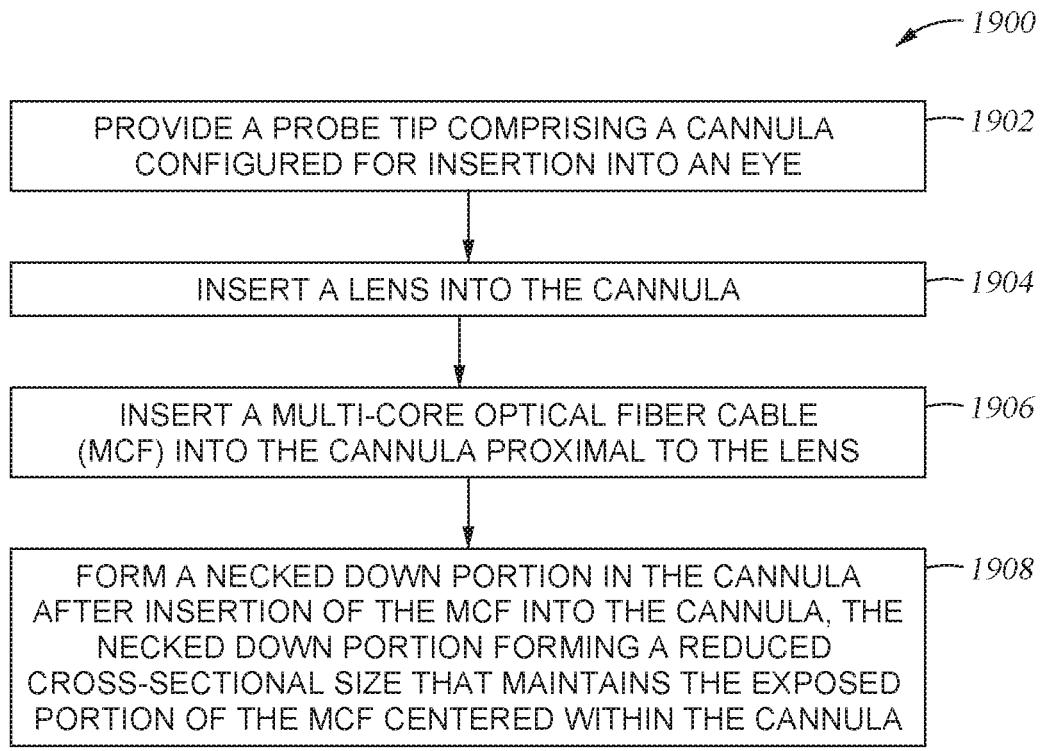
FIG. 19 illustrates example operations for producing a multi-spot laser probe, in accordance with a particular embodiment of the present invention.

FIG. 19 illustrates example flow chart 1900, which illustrates steps in a method for producing a multi-spot laser probe, in accordance with a particular embodiment of the present invention.

At block 1902, a probe tip is provided, which comprises a cannula configured for insertion into to an eye. For example, a technician or a machine may provide probe tip 901 having cannula 1702, as shown in FIG. 18.

At block 1904, a lens is inserted into the cannula. For example, lens 908 is inserted into cannula 1702.

At block 1906, an MCF is inserted into the cannula proximal to the lens. For example, MCF 900 is inserted into cannula 1702 proximal to lens 908, the MCF 900 comprising a plurality of cores 933. As shown, MCF 900 comprises cladding 932, shown at the exposed end 938 of MCF 900.

At block 1908, a necked down portion is formed in the cannula, the necked down portion forming a reduced cross-sectional size that maintains the exposed portion of the MCF centered within the cannula. For example, the necked down portion 1752 is formed in the cannula 1702.

Although several of the figures described herein show probes having protective windows, it is understood that the protective windows may be omitted. It is further within the scope of the present disclosure that the ends of the lens and/or protective windows may be a shape other than flat. For example, one or more of the distal and proximal ends of the lens and protective window may have a convex shape, as described herein.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A multi-spot laser probe comprising:
    a probe body shaped and sized for grasping by a user;
    a probe tip comprising a cannula configured for insertion into an eye, the cannula comprising:
        an inner passage; and
        an inner surface that defines the inner passage;
    a multi-core optical fiber cable (MCF) extending at least partially through the inner passage of the cannula, the MCF comprising:
        a plurality of cores;
        a cladding surrounding and separating each core in the plurality of cores from each of the other cores in the plurality of cores such that laser beams traveling down the plurality of cores remain separated in their respective cores without entering any of the other cores of the plurality of cores, wherein a refractive index of one or more of the plurality of cores is greater than a refractive index of the cladding;
        a coating surrounding the cladding; and
        a distal end free of the coating and having a reduced diameter,
    an annular gap formed between the distal end of the MCF and the inner surface of the cannula; and
    a ring disposed within the annular gap to maintain concentricity of the distal end of the MCF with the inner passage of the cannula.

2. The multi-spot laser probe of claim 1, wherein the ring is formed of a polyimide or a metal.

3. The multi-spot laser probe of claim 1, wherein an inner diameter of the ring corresponds to an outer diameter of the distal end of the multi-core optical fiber cable.

4. The multi-spot laser probe of claim 1, wherein an outer diameter of the ring corresponds to an inner diameter of the inner passage of the cannula.

5. The multi-spot laser probe of claim 1, further comprising a lens disposed in the inner passage of the cannula, distal of the multi-core optical fiber cable.

6. The multi-spot laser probe of claim 5, wherein the lens is a graded-index (GRIN) lens.

7. The multi-spot laser probe of claim 5, wherein the distal end of the MCF abuts the lens with a positive pressure.

8. The multi-spot laser probe of claim 5, wherein the distal end of the MCF is separated from the lens by an air gap.

9. The multi-spot laser probe of claim 5, further comprising a window at least partially disposed in the inner passage of the cannula distal to and abutting the lens.

10. The multi-spot laser probe of claim 1, wherein the cladding and plurality of cores are configured to keep laser beams confined to the cores while traveling the length of the plurality of cores while allowing illumination light to travel through the cladding down the length of the plurality of cores.

11. The multi-spot laser probe of claim 1, wherein the cladding is in physical contact with each core of the plurality of cores.

\* \* \* \* \*